(12) United States Patent
Huo et al.

(10) Patent No.: US 6,361,561 B1
(45) Date of Patent: Mar. 26, 2002

(54) INJECTABLE INTRAOCULAR LENS

(75) Inventors: Peter P. Huo; Stephen Q. Zhou; Christine J. Y. Liau, all of Irvine, CA (US); Sverker Norrby, Leek (NL)

(73) Assignee: Pharmacia & Upjohn AB, Stockholm (SE)

( * ) Notice: Subject to any disclaimer, the term of this patent is extended or adjusted under 35 U.S.C. 154(b) by 0 days.

(21) Appl. No.: 09/416,995

(22) Filed: Oct. 13, 1999

Related U.S. Application Data

(63) Continuation-in-part of application No. 09/170,160, filed on Oct. 13, 1998, now Pat. No. 6,066,172.

(51) Int. Cl.$^7$ .................................................. A61F 2/16
(52) U.S. Cl. ...................................... 623/6.56; 523/113
(58) Field of Search .............................. 623/6.11, 6.13, 623/6.56; 525/474; 528/10; 523/107, 113; 264/1.1

(56) References Cited

U.S. PATENT DOCUMENTS

| | | | |
|---|---|---|---|
| 4,537,943 A | * | 8/1985 | Talcott ....................... 623/6.11 |
| 4,542,542 A | * | 9/1985 | Wright ....................... 623/6.11 |
| 4,608,050 A | * | 8/1986 | Wright et al. .............. 623/6.11 |
| 5,116,369 A | * | 5/1992 | Kishibiki et al. .......... 623/6.11 |
| 5,278,258 A | | 1/1994 | Gerace et al. |
| 5,316,704 A | | 5/1994 | Wang |
| 5,391,590 A | | 2/1995 | Gerace et al. |
| 5,411,533 A | | 5/1995 | Gerace et al. |
| 5,476,515 A | | 12/1995 | Kelman |
| 5,643,275 A | | 7/1997 | Blake |
| 5,702,441 A | | 12/1997 | Zhou |

FOREIGN PATENT DOCUMENTS

| | | |
|---|---|---|
| EP | 578 087 A2 | 4/1994 |
| FR | 2 309 599 | 4/1976 |
| WO | 9323476 | 11/1993 |

OTHER PUBLICATIONS

Noll, Walter; Eigenschaften Technischer Siliconole, 1969 (not translated).

* cited by examiner

*Primary Examiner*—Dinh X. Nguyen
(74) *Attorney, Agent, or Firm*—Oppenheimer Wolff & Donnelly LLP

(57) ABSTRACT

Polysiloxanes suitable for the preparation of intraocular lenses by a crosslinking reaction, having a specific gravity of greater than about 1.0, a refractive index suitable for restoring the refractive power of the natural crystalline lens and a viscosity suitable for injection through a standard cannula are provided. Moreover, injectable intraocular lens material based on these polysiloxanes and methods of preparing intraocular lenses by direct injection into the capsular bag of the eye are also disclosed.

57 Claims, No Drawings

INJECTABLE INTRAOCULAR LENS

RELATED APPLICATIONS

This application is a continuation-in-part of U.S. patent application Ser. No. 09/170,160, filed Oct. 13, 1998, now U.S. Pat. No. 6,066,172.

FIELD OF INVENTION

The present invention relates to an intraocular lens and to materials useful in maling intraocular lenses (IOLs), specifically, injectable IOLs and methods for their preparation. More particularly, the invention relates to high specific gravity silicone materials suitable for making accommodative IOLs, which can be injected into the capsular bag with greater convenience than previously suggested materials.

BACKGROUND OF THE INVENTION

The human eye is a highly evolved and complex sensory organ. It is composed of a cornea, or clear outer tissue which refracts light lays enroute to the pupil, an iris which controls the size of the pupil thus regulating the amount of light entering the eye, and a lens which focuses the incoming light Through the vitreous fluid to the retia. The retina converts the incoming light into electrical energy that is transmitted through the brain stem to the occipital cortex resulting in a visual image. In the perfect eye the light path from the cornea, through the lens and vitreous fluid to the retina is unobstructed. Any obstruction or loss in clarity within these structures causes scattering or absorption of light rays resulting in diminished visual acuity. For example, the cornea can become damaged resulting in oedema, scarring or abrasions, the lens is susceptible to oxidative damage, trauma and infection, and the vitreous can become cloudy due to hemorrhage or inflammation.

As the body ages, the effects of oxidative damage caused by environmental exposure and endogenous free radical production accumulate resulting in a loss of lens flexibility and denatured proteins that slowly coagulate reducing lens transparency. The natural flexibility of the lens is essential for focusing light onto the retina by a process referred to as accommodation. Accommodation allows the eye to automatically adjust the field of vision for objects at different distances. A common condition known as presbyopia results when the cumulative effects of oxidative damage diminish this flexibility reducing near vision acuity. Presbyopia usually begins to occur in adults during their mid-forties; mild forms are treated with glasses or contact lenses.

Lenticular cataract is a lens disorder resulting from the further development of coagulated protein and calcification. There are four common types of cataracts: senile cataracts associated with aging and oxidative stress, traumatic cataracts which develop after a foreign body enters the lens capsule or following intense exposure to ionizing radiation or infrared rays, complicated cataracts which are secondary to diseases such as diabetes mellitus or eye disorders such as detached retinas, glaucoma and retinitis pigmentosa, and toxic cataracts resulting from medicinal or chemical toxicity. Regardless of the cause, the disease results in impaired vision and may lead to blindness.

Treatment of severe lens disease requires the surgical removal of the lens involving phakoemulsification followed by irrigation and aspiratio. However, without a lens the eye is unable to focus the incoming light on the retina. Consequently, an artificial lens is used to restore vision. Three types of prosthetic lenses are available: cataract glasses, external contact lenses and IOLs. Cataract glasses have thick lenses, are uncomfortably heavy and cause vision artifacts such as central image magnification and side vision distortion. Contact lenses resolve many of the problems associated with glasses, but require frequent cleaning, are difficult to handle (especially for elderly patients with symptoms of arthritis), and are not suited for persons who have restricted tear production. Intaoclar lenses are used in the majority of cases to overcome the aforementioned difficulties associated with cataract glasses and contact lenses.

IOLs mentioned in the prior art literature usually belong to one the following categories: non-deformable, foldable, expansible hydrogels and injectable. The earliest IOLs coming into surgical practice are non-deformable implants having rigid structures composed of acrylates and methaacrylates. This type of lenses requires a large surgical incision in the capsular bag and is not accommodative. The large incision results in protracted recovery times and the likelihood of introducing astigmatis. In an effort to reduce recovery time and patient discomfort numerous small incision techniques and lenses have been developed.

Present IOLs designed for small incision implantation have elastomeric characteristics and are made of silicone materials. This type of lenses can be rolled or folded, inserted into the capsular sac then unfolded once inside. Occasionally, the folding of the lens before insertion results in permanent deformation adversely effecting the implant's optical qualities. Foldable lenses meet the requirement of reducing the large surgical incision non-deformable lenses required, but are not accommodative. Moreover, both non-deformable and foldable IOLs are susceptible to mechanical dislocation resulting in damage to the corneal endothelium.

It has further been suggested to use an elastomeric polymer that becomes pliable when heated to body temperature or slightly above in small incision IOL implantation. Once pliable, such a lens would be deformed along at least one axis reducing its size sufficient for easy insertion through a small incision. The lens is then cooled to retain the modified shape until re-heated. The cooled lens is inserted into the capsular sac and the natural body temperature warms the lens and it returns to its original shape. The primary drawback to the thermoplastic lens is the limited number of polymers that meet the exacting needs of this approach. Most polymers are composed of polymethylacrylate which have solid-liquid transition temperatures above 100° C. To reduce these transition temperatures modifications of the polymer substrate with the use of plasticizers is required which eventually may leach into the eye.

Dehydrated hydrogels have also been suggested for small incisions techniques. Hydrogel lenses are dehydrated before insertion and naturally rehydrated once inside the capsular sac. However, once fully rehydrated the polymer struggle is notoriously weak due to the large amount of water absorbed. The typical dehydrated hydrogel's diameter will expand from 3 mm to 6 mm resulting in a lens that contains about 85% water. At this water concentration the refractive index drops to approximately 1.36 which is unacceptable for an IOL. To achieve a refractive index equal or greater than that of the natural lens (>1.40) a significantly thicker lens is required; this is even further exacerbated when lens diameters exceed 6 mm.

To further develop IOLs and reduce surgical incisions to below 1.5 mm, techniques with injectable IOLs have been suggested, wherein the low viscosity lens material is directly injected into the empty capsular bag and cured in situ as a part of the surgical procedure. In this process the capsular bag is to be used as a mold to form the shape of the lens and thereby contribute control its refraction. There have been several attempts to develop materials suitable for use as injectable IOLs. For example, Gerace et al. describe a fast curing mixture of vinyl-containing polyorganosiloxane, organosilicone comprising hydride groups and a platinum group metal catalyst used to form an IOL in their U.S. Pat. Nos. 5,278,258, 5,391,590 ('590) and 5,411,553. The resulting polymers demonstrate a reduced tendency of discoloration compared to other platinum catalyzed silicone polymers. The '590 patent also discloses a substantially nonfunctional polymer component of the mixture that has a viscosity at least 50 times greater than the functional polymers. The non-functional component is mixed with the functional components to adjust viscosity to a predetermined specification. Kelman discloses an injectable collagen IOL in U.S. Pat. No. 5,476,515. This lens is clear, resistant to epithelialation and is capable of accommodation. It is made from a transparent collagen compound that has a refractive index range from 1.2 to 1.6 that can be used in either its original viscous state, or polymerized into a soft gel. The collagen compound is injected directly into the capsular sac following natural lens removal.

Apart from problems with obtaining control over the crosslinking process and finding clinically acceptable conditions, there have been a struggle to perfect the polyorganosiloxane compositions, since they need to have a suitable viscosity for injection, a suitably high refractive index as well as suitable mechical characteristics after crosslinking, i.e. a suitable modulus. Polydimethylsiloxane (PDMS) has been employed as a material in foldable IOLs and has refractive index similar to that of the natural crystalline lens. This material is also exemplified as a part of the injection mixture in the above mentioned patents to Gerace et al. PDMS has also been found to have a relatively low viscosity and thereby a tendency to leak out of out of the desired injection site (i.e. the capsular bag). This is considered in the mentioned U.S. Pat. No. 5,391,590, wherein an additional high viscosity polysiloxane is added to the injection mixture. However, high viscosity silicones have the drawback in that they can entrap air bubbles, which can impair the optical quality of the resulting product. In addition, it has been found that polyorganosiloxanes having a high fraction of dimethylsiloxane units may have an unacceptable low specific gravity with the undesired result that the injected lens material will float on an aqueous layer in the capsular bag. In such a case, it will be difficult to fill the capsular sac completely and requires the surgeon to manually express water in order to maintain the correct lens shape during the curing process. Therefore, it is desirable to formulate an injectable lens forming material from polysiloxanes which can overcome the problems with floating and leakage, while still having a suitably high refractive index and the desirable mechanical and optical qualities so as to constitute an optimal replacement for the natural lens. These features are accomplished by the presently invented injectable lens material with a specific gravity greater that 1.0 which maintains a sufficiently high refractive index at least similar to that of natural lenses and provides for an optically smooth surface of the resulting lens.

OBJECTS AND SUMMARY OF THE INVENTION

The objects of the present invention are to provide injectable materials useful in making IOLs, specifically, injectable IOLs, and methods for their preparation and use. In particular it is an object of the present invention to provide intraocular lenses having the advantage of a specific gravity greater than 1.0 that greatly simplifies injection of the lens forming silicone material and helps to assure proper positioning and conformation once cured in situ, while yet being able to provide a controllable refractive index within the physiological range the recipient requires for proper vision and suitably low modulus of the cured product, so as to better replicate the accommodative characteristics of the implanted lens. A further object is to provide materials and methods that lead to a fully cured injectable IOL with an optically smooth surface. These and other objects not specifically enumerated are addressed by identifing high specifc gravty silicone materials suitable for making accommodative IOLs that can be injected with greater convenience than current materials.

In its most general form the present invention relates to polysiloxanes suitable for the preparation of intraocular lenses by a crosslinkig reaction, havng a specific gravity of greater than about 1.0, a refractive index suitable for restoring the refractive power of the natural crystalline lens and a viscosity suitable for injection through a standard cannula. It is to be understood that the polysiloxanes comprise a certain amount of functional unsaturated groups suitable for reaction with silicone bonded hydride (Si—H) groups in the presence of a catalyst. The skilled person knows of a large nunber of different alkenyl moieties and routes of how to synthesize vinyl functional polysiloxanes. A suitable and commonly employed route is to introduce end-blocking groups of vinyldimethyl siloxane wherein the olefinic vinyl group will enable curing by crosslinking. The polysiloxanes according to the invention can have refractive index ranges between 1.382 and up to about 1.60, preferably between from about 1.38 to 1.46 and more preferably index ranges from about 1.38 to 1.43, in order to be suitable as a material for the production of intraocular lenses. Most preferably, the inventive polysiloxanes have a specific gravity within the range of about 1.03 to about 1.20. The polysiloxanes should also have a suitable viscosity to be readily injectable tbrough conventional cannula having an 18 Gauge needle dimension or finer dimensions. Preferably, the polysiloxanes should be able to pass through a 21 Gauge needle. To comply with these criteria of injectability, polysiloxanes according to the present invention should have a viscosity less than about 60 000 cSt. More preferably, the viscosity should be less than about 8000 cSt. The skilled person will be able to relate these requirements to suitable degrees of polymerization.

The polysiloxanes typically consist essentially of different siloxane monomer units having the general formula —$R_aR_bSiO$—, wherein $R_a$ and $R_b$ are the same or different substituted or unsubstituted alkyl or aryl groups bound to the silicone atom. In accordance with the present invention at least one of the siloxane monomers included in the polysiloxanes has specific gravity greater than about 1.0. According to one aspect of the invention the polysiloxanes has at least one monomer, wherein $R_a$ and $R_b$ are the same or different alkyl or aryl groups of which at least one of said groups is substituted with one or several fluorine atoms. Preferably, the polysiloxanes comprises monomer units, wherein $R_a$ is fluoroalkyl and $R_b$ is alkyl and most preferably the polysiloxanes comprise 3,3,3-tifluoropropylmethylsiloxane monomers. In order to provide the polysiloxanes with the typically high specific gravity, it is preferred that the fluoroalkyl containing monomers exceed about 4 mol%. Further, it is also preferable that one of the siloxane monomers is an arylsiloxane and especially preferred arylsiloxanes are diphenylsiloxane and phenylalkylsiloxane. According to an aspect of the invention, the polysiloxanes essentially are terpolymers derived from three different siloxane monomers of the general formula $(R_1R_2SiO)_l$ $(R_3R_4SiO)_m$ $(R_5R_6SiO)$, wherein one of the three monomers has a specific gravity greater than about 1.0 and said terpolymer has a refctive index of about 1.41. In order to accomplish polysiloxanes with the mentioned requirements which the inventors have found to be advantageous for obtaining a material suitable for being injected into the capsular bag of the eye, it has been found suitable that $R_1$ and $R_2$ are the same or different lower substituted or unsubstituted alkyl and most preferable both are methyl. $R_3$ and $R_4$ shall be selected among the same or different substituted or unsubstituted aryl and alkyl groups, preferably $R_3$ is phenyl and $R_4$ is phenyl or methyl. $R_5$ and $R_6$ shall be selected among fluoroalkyl and alkyl groups and preferably $R_5$ is trifluoropropyl and $R_6$ is methyl. Alternatively, the inventive polysiloxanes can be higher polymers than terpolymers including but not limited to tetracopolymers with the same monomer types as mentioned.

According to preferred aspect of the invention, polysiloxanes essentially are vinyl-terminated terpolymers having the formula:

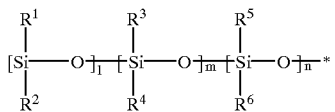

wherein $R^1$ and $R^2$ are independently $C_1$–$C_6$ alkyl; $R^3$ is phenyl; $R^4$ is phenyl or $C_1$–$C_6$ alkyl; $R^5$ is $CF_3(CH_2)_x$ wherein x is 1–5; $R^6$ is $C_1$–$C_6$ alkyl or fluoroalkyl; 1 is in the molar fraction range of 0 to 0.95; m is in the molar fraction range of 0 to 0.7; and n is in the molar fraction range of 0 to 0.65. It is preferred that $R^1$ is methyl, that $R^2$ is methyl, $R^4$ is phenyl, that x is 2, either independently, or in combination. Preferably according to these alternatives $R^6$ is methyl. According to one embodiment, the polysiloxane is a copolymer of diphenyl or phenylalkyl siloxane and dialkyl siloxane. According to further embodiments, the polysiloxane is a copolymer of diphenyl or phenylalkyl siloxane and trifluoroalkyl(alkyl)siloxane, or a terpolymer or higher order polymer of diphenyl and/or phenylalkyl siloxane, dialkyl siloxane and trifluoroalkyl alkyl siloxane. According to a specific preferred embodiment, polysiloxane is a terpolymer of dimethyl siloxane, diphenyl siloxane or phenylmethyl siloxane and 3,3,3-trifluoropropylmethyl siloxane. Preferably, said polysiloxanes comprise at least about 4 mol% of trifluoropropylmethyl siloxane and 1 to 50 mol% of diphenylsiloxane and/or phenylmethylsiloxane. More preferably said polysiloxanes comprise about 4 to 65 mol% 3,3,3 trifluoropropylmethyl siloxane, 1 to 50 mol% of diphenylsiloxane and dimethylsiloxane monomer units. One suitable polysiloxane composition for being a part of a composition for injection into the capsular bag of the human eye for the formation of IOL comprises about 28 mol% trifluoropropylmethyl siloxane, about 4 mol% diphenyl siloxane and dimethyl siloxane monomer units.

An important part of the present invention is the provision of an injectable lens material, comprising polysiloxanes having a specific gravity that is greater than about 1.0 and a refractive index of a natural lens which are defined as above, a crosslining agent having a suitable amount of urreacted Si—H groups and a catalyst. It is to be understood by the skilled person that such a material is prepared by mixing the a formulation of the polysiloxane and catalyst with a formulation of the crosslinking agent, just prior to its use. It is also to be understood that these formulations can comprise further conventional constituents, such as agents for affecting the crosslinking and agents commonly associated with the production of IOLs from silicone materials, e.g. UV light absorbers.

The catalysts can be found among platinum group metal containing catalysts commonly employed for catalyzing the formation of bonds between Si—H groups and vinyl groups as referred to in U.S. Pat. No. 5,278,258.

The crosslinking agents are of the siloxane or polysiloxane (i.e. a multifunctional organohydrogenpolysiloxane) type carrying at least two, preferably at least three Si—H groups, as disclosed in U.S. Pat. Nos. 5,278,258 and 5,444,106 which documents are incorporated as references for the crosslinking process. Other suitable crosslinkers are the branched siloxanes mentioned in U.S. Pat. No. 2,877,255. An example of a particularly suitable crosslinking agent for the present invention is tetrakis(dimethylsiloxy)silane.

The amounts of the components of the injectable material can be varied in accordance to the specific conditions. For example it is desirable to have reasonable fast curing process at ambient body temperature so final curing is accomplished within about 2 to 6 hours and that the injected composition is gelled into a stable polymeric network within a suitable working time for the surgeon. The skilled person will be able find suitable variation of the amount of the components and selecting suitable catalysts and crosslinking agents to obtain a suitable crosslinking density and so the resulting lens quality not will be compromised from any optical deficiency, such as discoloration from excessive catalyst levels. Examples of preferred routes to produce IOLs of the inventive lens material bases on specific polysiloxanes are given below.

The high specific gravity polysiloxanes preferably are prepared from a mixture of siloxane compounds including, either trimers, tetramers, or higher order cyclic siloxanes. The monomers used in the preferred embodiments of the present invention include, but are not limited to, methyl and substitated methyl siloxanes, phenyl siloxanes and trifluoropropyl methylsiloxanes having individual specific gravities ranging between about 0.97 and 1.28.

A crosslinkable terpolymeric silicone fluid, suitable for IOL can be prepared by copolymerizing three or more siloxane monomers in a predetermined ratio. Once formed the polymer has a specific gravity greater than 1.0 and can be injected into the patient's previously prepared capsular bag in a mixture with a crosslinker, the necessary catalyst and inhibitor formulation and cured in situ. During the early, i.e. gelation, phase of the curing process intraocular pressure is maintained to assure proper lens positioning and conformation within the capsular sac. The resulting IOL will have a refactive index within the physiologic range previously determined optimum for the given application and an optically smooth surface.

DETAILED DESCRIPTION OF EXEMPLARY EMBODIMENTS

The types of siloxane monomers useful in preparing the IOLs of this preferred embodiment include, but are not limited to, methyl and substituted methyl siloxanes, phenyl siloxanes and trifluoropropyl methyl siloxanes with individual specific gravities ranging between 0.97 and 1.28. The high specific gravity silicone co-polymers of the present invention are prepared by mixing a plurality of these compounds in a predetermined ratio to achieve a desired specific gravity and refractive index.

According to one embodiment, three siloxane monomers are mixed together with a suitable end blocker and dried in a reduced atmosphere under controlled thermal conditions. The reaction mixture is then catalyzed to induce co-polymerization in an inert atmosphere. The reaction is allowed to continue for a predetermined time in a precise thermal environment then terminated. Neat, the reaction product is washed, precipitated and dried. The specific gravity, refractive index and mean molecular weight are determined.

In another embodiment of the present invention three siloxane monomers are mixed together with a suitable end blocker and dried in a reduced atmosphere under controlled thermal conditions as before. The reaction mixture is then catalyzed to induce co-polymerization in an inert atmosphere. The reaction is allowed to continue for a predetermined time in a precise theral environment then terminated. Next, the reaction product is washed, precipitated and dried. The resulting precipitate is then re-dissolved in a suitable solvent and filtered to enhance clarity. The specific gravity, refractive index and mean molecular weight are deterrined. Changes in the reactants, their relative concentrations and reaction conditions will result in a variety of end products with different specific gravities and refractive indices. The benefits of these differences will become apparent to one skilled in the art from the specific examples below.

According to the methods of the present invention, the ratio of siloxane monomer reactants necessary to achieve a desired refractive index and specific gravity can be approximated mathematically. If N is the desired IOL's refractive index and P is the specific gravity of the lens' copolymer and where $n_{1-3}$ are the refractive indices and $p_{1-3}$ are the specific gravities of the monomer reactants then the following mathematical relationship can be used:

$$N=x_1n_1+x_2n_2+x_3n_3$$

$$P=x_1p_1+x_2p_2+x_3p_3$$

Where $x_{1-3}$ represent the ratio of the individual siloxane monomer reactants required to achieve an IOL with the desired optical and physical properties and $x_1+x_2+x_3=1$.

Having an injectable silicone lens with a specific gravity greater than 1.0 will greatly simplify the injection process and presents a significant improvement over previously suggested materials for injectable lens materials. Prosthetic lenses node by the process described herein are compliant and retain the refractive index of the natural lens making them ideal as corrective lenses as well as replacements for damaged and cataractous lenses.

The present invention improves considerably on previously suggested polysiloxane based materials for injectable IOLs due to its increased specific gravity to above 1.0, so displace residual water after its injection into the capsular sac's aqueous environment. This characteristic will reduce post-injection manipulation of the surgeon and will assure that the lens will assume a natural position and configuration. In accordance with the methods of the present invention an injectable IOL material is formed that greatly simplifies the injection, positioning and curing process. By the mentioned selection of siloxane monomers a high density injectable material can be provided with a controlled suitable refractive index comparable to that of the natural lens without compromising the other important requirements including a viscosity suitable for injection. This will greatly contribute to that is possible to adjust the refractive outcome of the injected lens formed with the capsular bag as a mold by having suitable fractions of siloxane units contributing to a high refractive index and siloxane units contributing to a high density. Another advantage of this invention is that extremely compliant nature fully cured lenses can be obtained. If a conventional foldable silicone lens is considered to have a stiffness of 100, a cured injectable lens made from the material of the present invention could be designed to have a stiffness ranging from zero to five. Therefore, lenses made from the material described herein can be accommodative and respond naturally to the changes in the eyes'to shape as focal length is adjusted. The accommodative nature of lenses fabricated from materials of the present invention would make them particularly suitable for corrective purposes besides replacements for diseased natural lenses and is considered within the scope of this invention. An unexpected, and beneficial, advantage of the present invention is the optically smooth surface formed after the lens has cured in situ.

The following examples are offered as being illustrative of the principles of the present invention and not by way of limitation.

EXAMPLE 1

Preparation of poly(dimethyl-co-methylphenyl-co-trifluoropropylmethyl)siloxane

To a dry 50 ml flask were added siloxane monomers: hexamethylcyclotrisiloxane, 6.0 g, 3,3,3-trifluoropropylmethylcylclotrisiloxane, 7.3 g, 1,3,5-timethyl-1,3,5-triphenylcyclotrisiloxane, 1.7 g (1.55 ml), and an end-blocker, 1,3-divinyltetramethyldisiloxane, 0.14 g (0.17 ml). The mixture was dried under vaccuum at 80° C. for 30 minutes, then purged with argon. The temperature was raised to 140° C. and potassium silanolate catalyst, 7 mg, was added to initiate polymerization. The reaction proceeded quickly as indicated by an increase in viscosity. After about 30 minutes the mixture clarified. After about 3 hours the temperature was raised to 160° C. and the reaction continued for a further 3 hours, after which the reaction was cooled to room temperature. The polymer was cleaned using a procedure of dilution with tetrahydrofuran and precipitation in methanol then dried. The dried silicone product was glass clear, with refractive index: 1.4070 (calculated: 1.410), specific gravity: 1.116 (calculated: 1.104), and molecular weight by GPC 25,000. Crosslinking of the polymer produced a clear silicone gel.

EXAMPLE 2

Prepartion of poly(dimethyl-co-methylphenyl-co-trifluoropropylmethyl)siloxane

A reaction mixture was prepared according to Example 1 except that the siloxane monomers were hexamethylcyclotrisiloxane, 9.0 g, 3,3,3-trifluoropropylmethylcylclotrisiloxane, 4.65 g, 1,3,5-trimethyl-1,3,5-triphenylcyclotrsiloxane, 1.35 g (1.23 ml). The resulting silicone polymer product was glass clear, the refractive index was 1.4082 (calculated: 1.410), specific gravity was 1.066 (calculated: 1.056) and the molecular weight by GPC was 26,000.

EXAMPLE 3

Preparation of poly(dimethyl-co-diphenyl-co-trifluoropropylmethyl)siloxane

To a dry 50 ml flask were added siloxane monomers: hexamethylcyclotrisiloxane, 7.5 g, 3,3,3-trifluoropropylmethylcylclotrisiloxane, 6.66 g, hexaphenylcyclotrisiloxane, 1.68 g, and an end-blocker, 1,3-divinyltetramethyldisiloxane, 0.28 g (0.34 ml). The mixture was dried under vacuum at 80° C. for 30 minutes, then purged with argon. The temperature was raised to 140° C. and potassium silanolate catalyst, circa 7 mg, was added to initiate polymerization. The reaction proceeded quickly as indicated by an increase in viscosity. After about 30 minutes the solution was almost clear with some residue at the bottom of the reaction vessel. The viscosity of the reaction mixture was decreasing. After about 2 hours the temperature was raised to 160° C. and the reaction continued for a further 3 hours, after which the reaction was cooled to room temperature. The polymer was washed with tetrahydrofuran and precipitated in methanol, then dried. The dried silicone product was slightly hazy. The material was dissolved in tetrahydrofuran, filtered through a 0.45 micrometer filter, and again dried, yielding a glass clear silicone polymer. The refractive index was 1.4095 (calculated: 1.424), specific gravity was 1.10 (calculated: 1.094) and the molecular weight by GPC was 18,000. Crosslinking of this material yielded a clear silicone gel.

EXAMPLE 4

Preparation of poly(dimethyl-co-diphenyl-co-trifluoropropylmethyl)siloxane

To a dry 1000 ml flask were weighed in order: octaphenylcyclotetrasiloxane, 90.61 g, 3,3,3-trifluoropropylmethylcylclotrisiloxane, 101.88 g, octamethylcylotetrasiloxane, 368.27 g, and an α,ω-divinyl dimethylsiloxane oligomer end-blocker (Mn 1287 by NMR analysis), 40.93 g. The flask was equipped for reflux and the reagents dried under vacuum on a bath at 80° C. for 30 minutes. The system was purged with nitrogen, and potassium silanolate (Mn 395), 267 mg, added. The bath temperature was increased to 160° C. and the mixture heated and stirred for 20 hours, yielding a clear colourless polymer mixture. After cooling, the product was diluted with 420 ml dichloromethane, and washed four times with 420 ml portions of water, the first portion being acidified with 3.0 ml of 0.1 N HCl and the second portion with 0.6 ml 0.1N HCl (the third and fourth portions were not acidified). The polymer was then washed twice with 420 ml portions methanol, diluted with 180 ml tetrahydrofuran, and washed twice more with methanol, as before. The solvent was then removed under vacuum over a few hours, with heating on a bath at 100° C., to a pressure of below 1 mbar. The polysiloxane product was clear and colourless, with refractive index 1.428 (calculated: 1.432) and density 1.04 (calculated: 1.043). Viscosity at 25° C. was 1802 cP. H-NMR, 500 MHz gave unit mole ratios: dimethyl/diphenyl/trifluoropropyl/divinyltetramethyl of 0.819/0.071/0.105/0.00494 (monomer ratios were: 0.827/0.070/0.099/0.00483), implying Mn 18,600. GPC gave Mn 18,500 and Mw 36,600.

EXAMPLE 5

Preparation of poly(dimethyl-co-diphenyl-co-trifluoropropylmethyl)siloxane

The polymerization method of Example 3 was repeated on a 125 g reagents scale, employing octaphenylcyclotetrasiloxane, 34.88 g, 3,3,3-trifluoropropylmethylcylclotrisiloxane, 25.25 g, octamethylcyclotetrasiloxane, 56.4 g, and an α,ω-divinyl dimethylsiloxane oligoner end-blocker (Mn 1287), 8.50 g, and potassium silanolate, 55 mg. The work-up differed fom Example 3, using chloroform, 57 ml, to dilute the polymer, followed by three washes with water and two with methanol, all 88 ml portions, then dilution with 44 ml tetrahydrofuran, followed by two more washes with 88 ml portions methanol, then vacuum stripping to <1 mbar on a bath at 100° C. The clear colourless product had refractive index 1.455 (calculated: 1.460) and density 1.08 (calculated: 1.080). Viscosity at 25° C. was 3324 cP. H-NMR, 500 MHz gave unit mole ratios: dimethyl/diphenyl/trifluorotopropyl/divinyltetramethyl of 0.697/0.158/0.140/0.00570 (monomer ratios were: 0.713/0.146/0.135/0.00549), implying Mn 18,600. GPC gave Mn 16,900 and Mw 33,400.

EXAMPLE 6

Curing of prepolymers

The silicone polymers were prepared for curing by formulating two parts, a Part A containing platinum catalyst in the form of the 1,3-divinyltetramethyldisiloxane complex, and a Part B containing crosslinker and siloxane inhibitor. The prefered crosslinker was tetrakisdimetylsiloxysilane, TKDMSS, but a polymeric silicon hydride (Gelest/ABCR HMS-151, a copolymer of methylhydrosiloxane and dimethylsiloxane having nominal Mn 1900–2000 and 15–18 mol% MeHSiO units) is here also reported for comparison. Optimum ratios of catalyst, crosslinker, and inhibitor were determined by studying the curing profiles of silicone mixtures using a rheometer (Rheometrics RDA 2, with determinaton of the moduli of the cured materials. Mixtures were formulated to give gel times circa 15–20 minutes at 20° C. Tests were performed at 35° C. using 25 mm diameter plates with 1 mm spacing. Frequency and stain sweeps were regularly performed on the materials. Mixtures for testing were prepared by accurately weighing portions of Parts A and B, mixing for 2 minutes, and degassing under reduced pressure before transferring the mixture to the plates. The disks obtained from the mixtures were clear and colourless. The results obtained are illustrated by the following examples:

EXAMPLE 6(a)

Prepolymer prepared in Example 4 was formulated as Part A, containing circa 8 ppm platinum, and Part B containing 18.2 mg TKDMSS/g Part B, plus siloxane inhibitor. The mixture was analysed on the rheometer in different weight ratios of B/A at 35° C., determining shear moduli, G', after 3000 seconds, at which time the mixtures were fully cured. The results for ratios B/A were: ratio: 0.86, G' 199.2 kPa; ratio: 1.00: G' 217.2 kPa; ratio: 1.15, G' 214.5 kPa.

EXAMPLE 6(b)

Prepolymer prepared as per Example 4 was formulated as Part A, containing circa 12 ppm platinum, and Part B containing 8.23% ww polymeric silicon hydride, Gelest/ABCR HMS-151, plus siloxane inhibitor. The mixture was analysed on the rheometer at 35° C. as above. Shear moduli, G', after 3000 seconds for ratios B/A were: ratio: 0.821, G' 100.7 kPa; ratio: 1.00: G' 167.9 kPa; ratio: 1.22, G' 193.2 kPa; ratio: 1.52, G' 184.0 kPa.

EXAMPLE 7

Implantation of silicone material into pig cadaver eyes

A fresh pig cadaver eye was prepared, with small aperture incision into the capsular bag and removal of the crystalline lens. The silicone composition was prepared from the prepolymer of Example 4, having refractive index 1.428, with Part A containing ca. 12 ppm platinum as a divinyltetramethyldisiloxane complex, and Part B containing tetrakisdimethylsiloxysilane crosslinker, 18.9 mg/g mixture, with siloxane inibitor. Gel time was circa 16 minutes at 20° C. Silicone for injection was prepared by mixing equal weights of Parts A and B in a Teflon pot, taking up in a syringe, vacuum degassing, and then injecting into the capsular bag via a 21 gauge cannula, so as to refill the bag and give appropriate curvature. After curing (ca. 45 minutes from the start of mixing) the lens was removed from the eye. The transparent tack-fee lens had anterior radius 10.1±0.4 mm, posterior radius 5±0.1 mm, thickness 5.33±0.03 mm, diameter 9.2±0.1 mm. Its power in air was 115±2 diopter, and focal length 8.7±0.1 mm (in water, lens power was 29.1±0.5 diopters, and focal length 45.7±0.8 mm). The natural crystalline lens of the pig has higher RI than that of the human lens. From the measured dimensions of 11 pig lenses it was calculated that an RI of circa 1.51 is required to restore natural refractive power in a refilled pig lens.

EXAMPLE 8

Implantation of silicone material into a human cadaver eye

A human cadaver eye was prepared, with small aperture incision into the capsular bag and removal of the crystalline lens. The silicone composition was prepared and a lens made as per Example 7. The transparent tack-free lens had anterior radius 8.7±0.5 mm, posterior radius 6.2±0.1 mm, thickness 4.11±0.06 mm, diameter 8.2±0.1 mm. Its calculated focal length, 49.08 mm gave a power in water of 27.1±0.7 diopters. The power in water of the average human lens is 21.8 diopters, and to have obtained this power in the lens refilled herein would have required filling material of RI 1.41.

What is claimed is:

1. Polysiloxanes suitable for the preparation of intraocular lenses by a crosslinking reaction, having a specific gravity of greater than about 1.0, a refractive index suitable for restoring the refractive power of the natural crystalline lens and a viscosity suitable for injection through a standard cannula.

2. Polysiloxanes according to claim 1, wherein the refractive index ranges between 1.382 up to about 1.60.

3. Polysiloxanes according to claim 2 comprising at least one siloxane monomer with a specific gravity greater than about 1.0.

4. Polysiloxanes according to claim 3 comprising at least one siloxane monomer—$R_aR_bSiO$—, wherein $R_a$ and $R_b$ are the same or different alkyl or phenyl groups of which at least one is substituted with one or several fluorine atoms.

5. Polysiloxanes according to claim 4 comprising fluoroalkyl(alkyl)siloxane monomers.

6. Polysiloxanes according to claim 5 comprising trifluoropropylmethylsiloxane monomers.

7. Polysiloxanes according to any of claims 1 to 6 being terpolymer or higher polymer of three or more siloxane monomer units.

8. Polysiloxanes according to any of claims 2 to 6 comprising arylsiloxane monomers.

9. Polysiloxanes according to claims 7 comprising arylsiloxane monomers.

10. Polysiloxanes according to claim 8 comprising methyl and substituted methylsiloxanes, phenylsiloxanes and trifluoropropylsiloxanes.

11. Polysiloxanes according to claim 9 comprising methyl and substituted methylsiloxanes, phenylsiloxanes and trifluoropropylsiloxanes.

12. Polysiloxanes according to claim 10 being essentially a terpolymer of
 a) dimethylsiloxane,
 b) methylphenylsiloxane or diphenylsiloxane;
 c) and trifluoropropylmethylsiloxane monomers.

13. Polysiloxanes according to claim 11 being essentially a terpolymer of:
 a) dimethylsiloxane,
 b) methylphenylsiloxane or diphenylsiloxane;
 c) and trifluoropropylmethylsiloxane monomers.

14. Polysiloxanes according to claim 7 comprising at least about 4 mol% trifluoropropylmethysiloxane.

15. Polysiloxanes according to any of claims 2 to 6 having a specific gravity of within the range of about 1.03 to 1.20 and refractive index from above about 1.38.

16. Polysiloxanes according to claim 7 having a specific gravity of within the range of about 1.03 to 1.20 and refractive index from above about 1.38.

17. Polysiloxanes according to claim 8 having a specific gravity of within the range of about 1.03 to 1.20 and refractive index from above about 1.38.

18. Polysiloxanes according to claim 9 having a specific gravity of within the range of about 1.03 to 1.20 and refractive index from above about 1.38.

19. Polysiloxanes according to claim 10 having a specific gravity of within the range of about 1.03 to 1.20 and refractive index from above about 1.38.

20. An injectable lens material, comprising polysiloxanes having a specific gravity that is greater than about 1.0 and a refractive index comparable to that of a natural lens according to any of claims 2–6, a crosslinking agent having a suitable amount of unreacted Si—H groups and a catalyst.

21. An injectable lens material, comprising polysiloxanes having a specific gravity that is greater than about 1.0 and a refractive index comparable to that of a natural lens according to claim 7, a crosslinking agent having a suitable amount of unreacted Si—H groups and a catalyst.

22. An injectable lens material, comprising polysiloxanes having a specific gravity that is greater than about 1.0 and a refractive index comparable to that of a natural lens according to claim 8, a crosslinking agent having a suitable amount of unreacted Si—H groups and a catalyst.

23. An injectable lens material, comprising polysiloxanes having a specific gravity that is greater than about 1.0 and a refractive index comparable to that of a natural lens according to claim 9, a crosslinking agent having a suitable amount of unreacted Si—H groups and a catalyst.

24. An injectable lens material, comprising polysiloxanes having a specific gravity that is greater than about 1.0 and a refractive index comparable to that of a natural lens according to claim 10, a crosslinking agent having a suitable amount of unreacted Si—H groups and a catalyst.

25. An injectable lens material, comprising polysiloxanes having a specific gravity that is greater than about 1.0 and a refractive index comparable to that of a natural lens according to claim 15, a crosslinking agent having a suitable amount of unreacted Si—H groups and a catalyst.

26. An injectable lens material, comprising polysiloxanes having a specific gravity that is greater than about 1.0 and a refractive index comparable to that of a natural lens according to claim 16, a crosslinking agent having a suitable amount of unreacted Si—H groups and a catalyst.

27. An injectable lens material, comprising polysiloxanes having a specific gravity that is greater than about 1.0 and a refractive index comparable to that of a natural lens according to claim 17, a crosslinking agent having a suitable amount of unreacted Si—H groups and a catalyst.

28. An injectable lens material, comprising polysiloxanes having a specific gravity that is greater than about 1.0 and a refractive index comparable to that of a natural lens according to claim 18, a crosslinking agent having a suitable amount of unreacted Si—H groups and a catalyst.

29. An injectable lens material, comprising polysiloxanes having a specific gravity that is greater than about 1.0 and a refractive index comparable to that of a natural lens according to claim 19, a crosslinking agent having a suitable amount of unreacted Si—H groups and a catalyst.

30. A reaction mixture for making polysiloxanes of an injectable lens material comprising a plurality of siloxane monomers having a specific gravity ranging from 0.97 to 1.28, wherein the siloxane monomers comprise one or more trimer or tetramer or higher order cyclic siloxane monomers forming a silicone lens material with a specific gravity greater than 1.0.

31. The reaction mixture of claim 30, wherein the plurality of siloxane monomers is copolymerized to make a terpolymer with a refractive index of about 1.41 and a specific gravity of about 1.1.

32. The reaction mixture of claim 31, wherein at least one of the monomers has a specific gravity that is greater than 1.0.

33. The reaction mixture of claim 31, wherein the plurality of siloxane monomers are selected from a group consisting of methyl and substituted methyl siloxanes, phenyl siloxanes and trifluoropropyl methyl siloxane.

34. The reaction mixture of claim 31, wherein the plurality of siloxane monomers consists essentially of cyclic dimethylsiloxane monomer, cyclic diphenylsiloxane monomer and 3,3,3- trifluoropropylmethyl cyclotrisiloxane.

35. The reaction mixture of claim 31, wherein the plurality of siloxane monomers consists essentially of cyclic dimethylsiloxane monomer, triphenyltrimethyl cyclosiloxane monomer and 3,3,3-trifluoropropylmethyl cyclotrisiloxane.

36. A method of preparing an intraocular lens, comprising:
    providing a reaction mixture according to any of claims 31 to 35;
    polymerizing the siloxane monomers to form a polysiloxane having a specific gravity greater than 1.0;
    transferring the polymerized siloxane monomers in a mixture together with a crosslinking agent and a catalyst to the capsular sac; and
    curing the mixture to the final lens.

37. A method of preparing an intraocular lens including the provision of a mixture comprising the polysiloxanes according to any of claims 1–6, a crosslinker and a catalyst, injecting the said mixture into a mold and curing said mixture at curing temperature optionally under forming pressure for a time sufficient to prepare said lens.

38. A method of preparing an intraocular lens including the provision of a mixture comprising the polysiloxanes according to claim 7, a crosslinker and a catalyst, injecting the said mixture into a mold and curing said mixture at curing temperature optionally under forming pressure for a time sufficient to prepare said lens.

39. A method of preparing an intraocular lens including the provision of a mixture comprising the polysiloxanes according to claim 8, a crosslinker and a catalyst, injecting the said mixture into a mold and curing said mixture at curing temperature optionally under forming pressure for a time sufficient to prepare said lens.

40. A method of preparing an intraocular lens including the provision of a mixture comprising the polysiloxanes according to claim 9, a crosslinker and a catalyst, injecting the said mixture into a mold and curing said mixture at curing temperature optionally under forming pressure for a time sufficient to prepare said lens.

41. A method of preparing an intraocular lens including the provision of a mixture comprising the polysiloxanes according to claim 10, a crosslinker and a catalyst, injecting the said mixture into a mold and curing said mixture at curing temperature optionally under forming pressure for a time sufficient to prepare said lens.

42. A method of preparing an intraocular lens including the provision of a mixture comprising the polysiloxanes according to claim 15, a crosslinker and a catalyst, injecting the said mixture into a mold and curing said mixture at curing temperature optionally under forming pressure for a time sufficient to prepare said lens.

43. A method of preparing an intraocular lens including the provision of a mixture comprising the polysiloxanes according to claim 16, a crosslinker and a catalyst, injecting the said mixture into a mold and curing said mixture at curing temperature optionally under forming pressure for a time sufficient to prepare said lens.

44. A method of preparing an intraocular lens including the provision of a mixture comprising the polysiloxanes according to claim 17, a crosslinker and a catalyst, injecting the said mixture into a mold and curing said mixture at curing temperature optionally under forming pressure for a time sufficient to prepare said lens.

45. A method of preparing an intraocular lens including the provision of a mixture comprising the polysiloxanes according to claim 18, a crosslinker and a catalyst, injecting the said mixture into a mold and curing said mixture at curing temperature optionally under forming pressure for a time sufficient to prepare said lens.

46. A method of preparing an intraocular lens including the provision of a mixture comprising the polysiloxanes according to claim 19, a crosslinker and a catalyst, injecting the said mixture into a mold and curing said mixture at curing temperature optionally under forming pressure for a time sufficient to prepare said lens.

47. A method according to claim 37, wherein the mixture is injected into the capsular bag of a human eye and cured at an ambient temperature.

48. A method according to claim 38, wherein the mixture is injected into the capsular bag of a human eye and cured at an ambient temperature.

49. A method according to claim 39, wherein the mixture is injected into the capsular bag of a human eye and cured at an ambient temperature.

50. A method according to claim 40, wherein the mixture is injected into the capsular bag of a human eye and cured at an ambient temperature.

51. A method according to claim 41, wherein the mixture is injected into the capsular bag of a human eye and cured at an ambient temperature.

52. A method according to claim 42, wherein the mixture is injected into the capsular bag of a human eye and cured at an ambient temperature.

53. A method according to claim 43, wherein the mixture is injected into the capsular bag of a human eye and cured at an ambient temperature.

54. A method according to claim 44, wherein the mixture is injected into the capsular bag of a human eye and cured at an ambient temperature.

55. A method according to claim 45, wherein the mixture is injected into the capsular bag of a human eye and cured at an ambient temperature.

56. A method according to claim 46, wherein the mixture is injected into the capsular bag of a human eye and cured at an ambient temperature.

57. A method according to claim 47, wherein the mixture is injected into the capsular bag of a human eye and cured at an ambient temperature.

* * * * *